(12) United States Patent
Lueninghoener

(10) Patent No.: US 12,156,885 B2
(45) Date of Patent: *Dec. 3, 2024

(54) METHODS AND COMPOSITIONS FOR TREATING HEART CONDITIONS

(71) Applicant: Catherine Lueninghoener, St. Louis, MO (US)

(72) Inventor: Catherine Lueninghoener, St. Louis, MO (US)

(*) Notice: Subject to any disclaimer, the term of this patent is extended or adjusted under 35 U.S.C. 154(b) by 0 days.

This patent is subject to a terminal disclaimer.

(21) Appl. No.: 17/541,533

(22) Filed: Dec. 3, 2021

(65) Prior Publication Data

US 2022/0193122 A1    Jun. 23, 2022

Related U.S. Application Data

(63) Continuation of application No. 17/009,275, filed on Sep. 1, 2020, now Pat. No. 11,219,642.

(51) Int. Cl.
*A61K 33/14*    (2006.01)
*A61K 45/06*    (2006.01)

(52) U.S. Cl.
CPC ............. *A61K 33/14* (2013.01); *A61K 45/06* (2013.01)

(58) Field of Classification Search
CPC ........ A61K 33/00; A61K 33/14; A61K 45/06; A61P 9/00; A61P 9/12; A61P 9/06
See application file for complete search history.

(56) References Cited

U.S. PATENT DOCUMENTS

| 9,675,585 B1 * | 6/2017 | Fix .............................. A61P 9/12 |
| 11,219,642 B1 * | 1/2022 | Lueninghoener .... A61K 31/138 |
| 2003/0228361 A1 | 12/2003 | Baichwal et al. |
| 2005/0032879 A1 | 2/2005 | Okarter |
| 2005/0070552 A1 | 3/2005 | Fedida et al. |
| 2009/0192392 A1 * | 7/2009 | Riobo Aboy .......... A61B 5/021 600/485 |
| 2010/0236926 A1 * | 9/2010 | Staal ................. B01L 3/502715 204/600 |
| 2018/0195128 A1 * | 7/2018 | Snyder ................. C12Q 1/6883 |
| 2020/0345744 A1 * | 11/2020 | Aronsen ............ A61K 31/4985 |

FOREIGN PATENT DOCUMENTS

| RU | 2700263 | 9/2019 |
| WO | WO 95/10289 | 4/1995 |

OTHER PUBLICATIONS

Dumovic et al., "Effect of Therapeutic Dosage of Lithium on the Heart" Br. J. Clin. Pharmac. 9:599-604 (1980).
Mohandas and Rajmohan, "Lithium use in special populations" Indian J Psychiatry 49(3): 211-18 (Jul.-Sep. 2007).
Tilkian et al., "Effect of Lithium on Cardiovascular Performance: Report on Extended Ambulatory Monitoring and Exercise Testing Before and During Lithium Therapy" The American Journal of Cardiology vol. 38, pp. 701-708 (Nov. 1976).
Finley, "Drug Interactions with Lithium: An Update" Clin. Pharmacokinet. 55(8): 925-41 (2016).
Juurlink et al., "Drug-Induced Lithium Toxicity in the Elderly: A Population-Based Study" J. Am. Geriatr. Soc. 52(5): 794-98 (2004).
Gaby et al., "Treatment of lithium tremor with metoprolol" American Journal of Psychiatry 140(5):593-95 (May 1983).
Lee et al. "Antiarrhythmic effect of lithium in rats after myocardial infarction by activation of Nfr2/HO-1 signaling" Free Radical Biology and Medicine 77:71-81 (Sep. 2014).
Eskalith rxlist.com Aug. 11, 2020 two pages.
Lithobid rxlist.com Aug. 5, 2020 two pages.

\* cited by examiner

*Primary Examiner* — Nicole P Babson
*Assistant Examiner* — John P Nguyen
(74) *Attorney, Agent, or Firm* — McDonnell Boehnen Hulbert & Berghoff LLP

(57) ABSTRACT

The disclosure provides methods and compositions for treating heart conditions. In particular, the disclosure provides compositions comprising lithium, or a salt thereof, either alone or in combination with at least one additional anti-arrhythmia agent, and methods for treating heart conditions using such compositions.

10 Claims, 1 Drawing Sheet

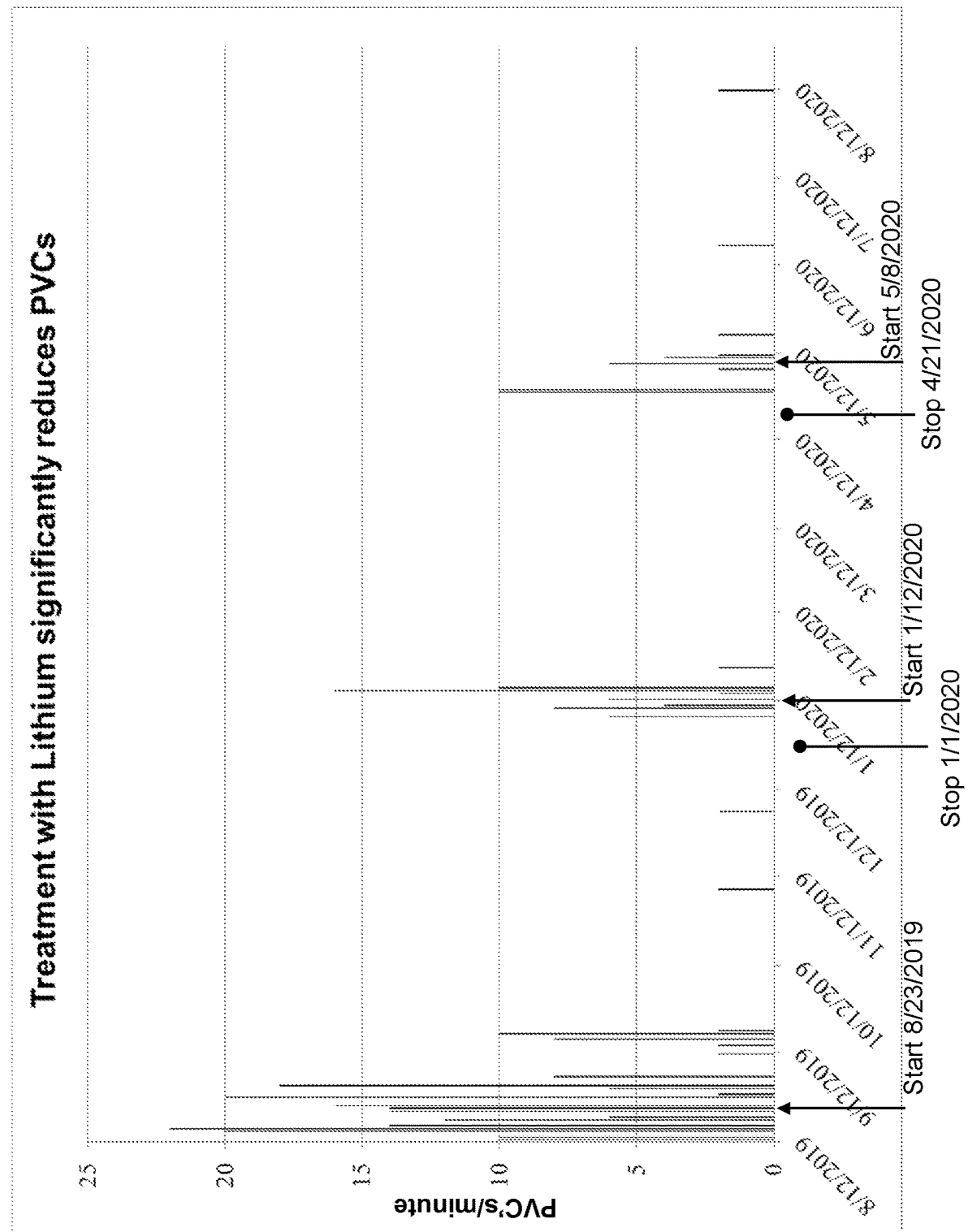

METHODS AND COMPOSITIONS FOR TREATING HEART CONDITIONS

RELATED APPLICATION

This application is a continuing application of U.S. application Ser. No. 17/009,275, filed Sep. 1, 2020, the entire content of which is hereby incorporated by reference in its entirety.

BACKGROUND

There are many types of heart disease, and each one has its own symptoms and treatment. Lifestyle changes and medicine can make a huge difference in improving a subject's health. One type of heart disease is an arrhythmia (when the heart has an irregular beating pattern). Serious arrhythmias can often develop from other heart problems, but may also happen on their own.

Treatment of arrhythmia depends on the type and severity of the arrhythmia. In some cases of arrhythmia, no treatment is necessary. Treatment options can include: medications, lifestyle changes, invasive therapies, electrical devices, and/or surgery. Some anti-arrhythmic medications are extremely toxic, and thus are very infrequently used for the treatment of arrhythmias, and even then can only be used for a short time due to the toxicity. Thus, there is a need in the art to develop improved methods, compositions, and therapies for treating cardiac arrhythmias.

SUMMARY

The disclosure provides methods and compositions for treating heart conditions. In particular, the disclosure provides compositions comprising lithium, or a salt thereof, either alone or in combination with at least one additional anti-arrhythmia agent, and methods for treating heart conditions using such compositions.

In one aspect, the disclosure provides a method for treating and/or preventing a heart condition, comprising administering an effective amount of lithium, or a salt thereof, to a subject in need thereof.

In certain embodiments of this aspect, the heart condition is premature ventricular contraction (PVC), ventricular premature contraction (VPC), ventricular tachycardia, ventricular fibrillation, paroxysmal supraventricular tachycardia, accessory pathway tachycardia, AV nodal reentrant tachycardia, supraventricular tachycardia, premature atrial contractions, atrial fibrillation, atrial flutter, trigeminy, bigeminy, or Wolff-Parkinson-White (WPW) syndrome. In one embodiment, the heart condition is premature ventricular contraction (PVC) or ventricular premature contraction (VPC). In another embodiment, the heart condition is atrial fibrillation.

In some embodiments, the lithium, or salt thereof, is lithium carbonate ($Li_2CO_3$), lithium sulfate ($Li_2SO_4$), lithium citrate ($Li_3C_6H_5O_7$), lithium acetate ($C_2H_3LiO_2$), lithium bromide (LiBr), lithium chloride (LiCl), lithium orotate ($C_5H_3LiN_2O_4$), or lithium gluconate ($C_6H_{11}LiO_7$). In certain embodiments, the effective amount of lithium comprises about 5 mg to about 1800 mg per day, about 10 mg to about 1200 mg per day, about 25 mg to about 600 mg per day, about 50 mg to about 550 mg per day, about 100 mg to about 500 mg per day, about 150 mg to about 450 mg per day, about 200 mg to about 400 mg per day, or about 250 mg to about 350 mg per day. In one embodiment, the effective amount of lithium comprises about 300 mg per day.

In some embodiments, the effective amount of lithium results in a lithium serum concentration in the subject in the range of about 0.01 to about 1.2 mmol/L, about 0.02 to about 1.0 mmol/L, about 0.05 to about 0.8 mmol/L, about 0.1 to about 0.6 mmol/L, about 0.2 to about 0.5 mmol/L, about 0.25 to about 0.45 mmol/L, or about 0.1 to about 0.3 mmol/L. In one embodiment, the effective amount of lithium results in a lithium serum concentration in the subject in the range of about 0.1 to about 0.3 mmol/L.

In some embodiments, the effective amount of lithium, or salt thereof, is administered as an extended release formulation. In certain embodiments, the effective amount of lithium, or salt thereof, is administered one time per day, two times per day, three times per day, or four times per day.

In some embodiments, the effective amount of lithium, or salt thereof, is administered orally, parenterally, transdermally, topically, transmucosally, by inhalation, by suppository, by buccal delivery, by sublingual delivery, by ophthalmic delivery, or by injection (subcutaneous injection, subdermal injection, intramuscular injection, depot administration, or intravenous injection).

In some embodiments, the subject is treated for about 1 month, about 2 months, about 3 months, about 4 months, about 5 months, about 6 months, about 7 months, about 8 months, about 9 months, about 10 months, about 11 months, about 1 year, about 2 years, or more than 2 years. In certain embodiments, the subject is treated indefinitely.

In some embodiments, the method further comprises administering an additional anti-arrhythmic agent. In certain embodiments, the additional anti-arrhythmic agent is a sodium channel blocker (Class I), a beta-blocker (Class II), a potassium channel blocker (Class III), a calcium channel blocker (Class IV), and/or another anti-arrhythmic agent.

In some embodiments, the additional anti-arrhythmic agent is a beta-blocker and the beta-blocker is Acebutolol (SECTRAL®), Atenolol (TENORMIN®), Betaxolol (KERLONE®), Bisoprolol (ZEBETA®, ZIAC®), Carteolol (CARTROL®), Carvedilol (COREG®), Labetalol (NORMODYNE®, TRANDATE®), Metoprolol (LOPRESSOR®, TOPROL-XL®), Nadolol (CORGARD®), Nebivolol (BYSTOLIC®), Penbutolol (LEVATOL®), Pindolol (VISKEN®), Propanolol (INDERAL®), Sotalol (BETAPACE®), or Timolol (BLOCADREN®).

In another aspect, the disclosure provides a composition comprising lithium, or a salt thereof, and an additional anti-arrhythmic agent.

In certain embodiments of this aspect, the lithium, or salt thereof, is lithium carbonate ($Li_2CO_3$), lithium sulfate ($Li_2SO_4$), lithium citrate ($Li_3C_6H_5O_7$), lithium acetate ($C_2H_3LiO_2$), lithium bromide (LiBr), lithium chloride (LiCl), lithium orotate ($C_5H_3LiN_2O_4$), or lithium gluconate ($C_6H_{11}LiO_7$).

In some embodiments, the additional anti-arrhythmic agent is a sodium channel blocker (Class I), a beta-blocker (Class II), a potassium channel blocker (Class III), a calcium channel blocker (Class IV), and/or another anti-arrhythmic agent.

In some embodiments, the additional anti-arrhythmic agent is a beta-blocker and the beta-blocker is Acebutolol (SECTRAL®), Atenolol (TENORMIN®), Betaxolol (KERLONE®), Bisoprolol (ZEBETA®, ZIAC®), Carteolol (CARTROL®), Carvedilol (COREG®), Labetalol (NORMODYNE®, TRANDATE®), Metoprolol (LOPRESSOR®, TOPROL-XL®), Nadolol (CORGARD®), Nebivolol (BYSTOLIC®), Penbutolol (LEVATOL®), Pindolol (VISKEN®), Propanolol (INDERAL®), Sotalol (BETAPACE®), or Timolol (BLOCADREN®).

In one embodiment, the lithium, or salt thereof, is lithium carbonate ($Li_2CO_3$), and the beta-blocker is Metoprolol (LOPRESSOR®, TOPROL-XL®). In another embodiment, the lithium, or salt thereof, is lithium sulfate ($Li_2SO_4$), and the beta-blocker is Metoprolol (LOPRESSOR®, TOPROL-XL®).

In some embodiments, the composition comprises about 50 mg, about 100 mg, about 150 mg, about 200 mg, about 250 mg, about 300 mg, about 350 mg, about 400 mg, about 450 mg, about 500 mg, or about 600 mg of the lithium, or salt thereof.

In some embodiments, the composition comprises about 2.5 mg, about 3.125 mg, about 5 mg, about 6.25 mg, about 10 mg, about 12.5 mg, about 20 mg, about 25 mg, about 30 mg, about 40 mg, about 50 mg, about 60 mg, about 80 mg, about 100 mg, about 150 mg, about 200 mg, about 250 mg, or about 300 mg of the additional anti-arrhythmic agent.

In some embodiments, the compositions as disclosed herein are extended release formulations.

BRIEF DESCRIPTION OF THE DRAWINGS

FIG. 1 shows that treatment with lithium significantly reduces PVCs in a patient. A patient with PVCs as documented with a cardiac event monitor was given lithium carbonate 300 mg per day ($L_{12}CO_3$ 150 mg BID) in combination with metoprolol 150 mg per day for three different trials. Trial 1 was started on Aug. 23, 2019 and stopped on Jan. 1, 2020; Trial 2 was started on Jan. 12, 2020 and stopped on Apr. 21, 2020; and Trial 3 was started on May 8, 2020 and was ongoing at the time the instant application was filed. Within a few days, PVCs were reduced by about 90% and were reduced throughout the duration of lithium treatment.

DETAILED DESCRIPTION

The disclosure provides methods and compositions for treating heart conditions. In particular, the disclosure provides compositions comprising lithium, or a salt thereof, either alone or in combination with at least one additional anti-arrhythmia agent, and methods for treating heart conditions using such compositions.

In one aspect, the disclosure provides a method for treating and/or preventing a heart condition, comprising administering an effective amount of lithium, or a salt thereof, to a subject in need thereof.

The term "subject" as used herein includes human and non-human animal subjects.

A "heart condition" or "heart disorder" is any condition that would benefit from treatment using the compositions as disclosed herein. "Heart disorder" and "heart condition" are used interchangeably herein and include chronic and acute disorders or diseases, and can include, but are not limited to, coronary artery disease (CAD), atherosclerosis, heart attack, stroke, heart failure, arrhythmia, heart valve problems, and/or other cardiovascular disease (e.g., conditions that involve narrowed or blocked blood vessels that can lead to a heart attack, chest pain, or stroke). In one embodiment, the heart condition can be an arrhythmia (i.e., a variation from a normal heart rate and/or heart rhythm that is not physiologically justified). In some embodiments, the heart condition can be an arrhythmia where electric impulses are initiated too early and/or disrupt a heart's normal rhythm. In some embodiments, the heart condition can be an arrhythmia where electric impulses originate from an area of the heart which is not considered normal, or which are conducted in an area or pathway of the heart which is not considered normal. In certain embodiments, the heart condition can include, but is not limited to, premature ventricular contraction (PVC), ventricular premature contraction (VPC), ventricular tachycardia, ventricular fibrillation, paroxysmal supraventricular tachycardia, accessory pathway tachycardia, AV nodal reentrant tachycardia, supraventricular tachycardia, premature atrial contractions, atrial fibrillation, atrial flutter, trigeminy, bigeminy, or Wolff-Parkinson-White (WPW) syndrome. In certain embodiments, the heart condition is atrial fibrillation or atrial flutter. In one embodiment, the heart condition is premature ventricular contraction (PVC) or ventricular premature contraction (VPC). The heart conditions of premature ventricular contraction (PVC) and ventricular premature contraction (VPC) both refer to the same heart condition of extra heartbeats that begin in one of the heart's ventricles. The extra beats disrupt regular heart rhythm, and sometimes cause a subject to feel a fluttering or skipped beat. Premature ventricular contraction (PVC) and ventricular premature contraction (VPC) can be used interchangeably, and in some instances can also be referred to as premature ventricular complexes, ventricular premature beats, or ventricular extrasystoles.

The terms "treatment" or "treat" as used herein can refer to both therapeutic treatment and prophylactic or preventative measures. Those in need of treatment include those having heart disease as well as those prone to have the heart disease or those in which the heart disease is to be prevented. In certain embodiments, the compositions as disclosed herein is administered to a subject in need of treatment once per day, twice per day, three times per day, four times per day, or more. In some embodiments, the treatment is administered as an extended release formulation. The appropriate dose, frequency, and duration can be modified to address the particular needs of a particular subject by taking into account factors including, but not limited to, the age, gender, weight, and health of the subject; the severity, extent, and type of the heart condition. In some embodiments, the length of treatment can be less than 1 week to 12 months, or more than 12 months. In certain embodiments, treatment duration can be indefinite. In some embodiments, treatment duration can be until disease remission.

As used herein, the term "lithium" refers to the chemical element lithium with the symbol Li and atomic number 3. In certain embodiments, lithium, or a salt thereof, can refer to any lithium composition that results in free lithium ($Li^+$) in the serum of a subject when administered to the subject. In some embodiments, the lithium, or salt thereof, is lithium carbonate ($Li_2CO_3$), lithium sulfate ($Li_2SO_4$), lithium citrate ($Li_3C_6H_5O_7$), lithium acetate ($C_2H_3LiO_2$), lithium bromide (LiBr), lithium chloride (LiCl), lithium orotate ($C_5H_3LiN_2O_4$), or lithium gluconate ($C_6H_{11}LiO_7$).

The terms "effective amount" and "therapeutically effective amount" when used in reference to a composition comprising lithium, or a salt thereof, refer to an amount or dosage sufficient to produce a desired therapeutic result. More specifically, a therapeutically effective amount is an amount of lithium, or a salt thereof, sufficient to prevent and/or inhibit, for some period of time, one or more of the clinically defined pathological processes associated with the heart disease being treated. For example, in a patient with an arrhythmia, an effective amount would result in disappearance of or a decrease in the arrhythmia in the patient. In another example, in a patient with PVCs, an effective amount would result in disappearance of or a decrease in the number of PVCs the patient experiences. In some embodiments, the therapeutically effective amount of lithium can be considered a low dose (e.g., a low dose when compared to a dose used as a psychiatric medication). The effective amount may vary depending on the lithium, or a salt thereof, dosages that are being used, and also depends on a variety of factors and conditions related to the patient being treated and the severity of the heart disease. For example, if the lithium, or a salt thereof, composition is to be administered in vivo, factors such as the age, weight, and health of the patient as well as dose response curves and toxicity data obtained in preclinical animal work would be among those factors considered in determining the effective amount or therapeutically effective amount to be administered. The determination of an effective amount or therapeutically effective amount of a given pharmaceutical composition is well within the ability of those skilled in the art.

In certain embodiments, the effective amount of lithium comprises about 5 mg to about 1800 mg, 10 mg to about 1200 mg per day, about 25 mg to about 600 mg per day, about 50 mg to about 550 mg per day, about 100 mg to about 500 mg per day, about 150 mg to about 450 mg per day, about 200 mg to about 400 mg per day, or about 250 mg to about 350 mg per day. In certain embodiments, the effective amount of lithium comprises about 5 mg per day, about 10 mg per day, about 15 mg per day, about 25 mg per day, about 50 mg per day, about 100 mg per day, about 150 mg per day, about 175 mg per day, about 200 mg per day, about 225 mg per day, about 250 mg per day, about 275 mg per day, about 300 mg per day, about 325 mg per day, about 350 mg per day, about 375 mg per day, about 400 mg per day, about 425 mg per day, about 450 mg per day, about 475 mg per day, about 500 mg per day, about 525 mg per day, about 550 mg per day, about 575 mg per day, about 600 mg per day, about 625 mg per day, about 650 mg per day, about 675 mg per day, about 700 mg per day, about 725 mg per day, about 750 mg per day, about 775 mg per day, about 800 mg per day, about 825 mg per day, about 850 mg per day, about 875 mg per day, about 900 mg per day, about 925 mg per day, about 950 mg per day, about 975 mg per day, about 1000 mg per day, about 1050 mg per day, about 1100 mg per day, about 1150 mg per day, about 1200 mg per day, about 1250 mg per day, about 1300 mg per day, about 1350 mg per day, about 1400 mg per day, about 1450 mg per day, about 1500 mg per day, about 1550 mg per day, about 1600 mg per day, about 1650 mg per day, about 1700 mg per day, about 1750 mg per day, or about 1800 mg per day. In one embodiment, the effective amount of lithium comprises about 300 mg per day.

In some embodiments, the effective amount of lithium results in a lithium ($Li^+$) serum concentration in the subject in the range of about 0.01 to about 1.2 mmol/L, about 0.02 to about 1.0 mmol/L, about 0.05 to about 0.8 mmol/L, about 0.1 to about 0.6 mmol/L, about 0.2 to about 0.5 mmol/L, about 0.25 to about 0.45 mmol/L, or about 0.1 to about 0.3 mmol/L. In certain embodiments, the effective amount of lithium ($Li^+$) serum concentration in the subject is about 0.01 mmol/L, about 0.02 mmol/L, about 0.04 mmol/L, about 0.05 mmol/L, about 0.075 mmol/L, about 0.1 mmol/L, about 0.2 mmol/L, about 0.25 mmol/L, about 0.3 mmol/L, about 0.35 mmol/L, about 0.4 mmol/L, about 0.45 mmol/L, about 0.5 mmol/L, about 0.55 mmol/L, about 0.6 mmol/L, about 0.65 mmol/L, about 0.7 mmol/L, about 0.75 mmol/L, about 0.8 mmol/L, about 0.85 mmol/L, about 0.9 mmol/L, about 0.95 mmol/L, about 1.00 mmol/L, about 1.1 mmol/L, or 1.2 mmol/L. In one embodiment, the effective amount of lithium results in a lithium serum concentration in the subject in the range of about 0.1 to about 0.3 mmol/L.

In some embodiments, the effective amount of lithium, or salt thereof, is administered in a single dose or in multiple doses. In some embodiments, the effective amount of lithium, or salt thereof, is administered as an extended release formulation. In certain embodiments, the effective amount of lithium, or salt thereof, is administered one time per day, two times per day, three times per day, or four times per day. Dosing frequency will depend upon the pharmacokinetic parameters of the composition being used. Typically, a clinician will administer the composition until a dosage is reached that achieves the desired effect. In some embodiments, the composition is administered about every 24, 23, 22, 21, 20, 19, 18, 17, 16, 15, 14, 13, 12, 11, 10, 9, 8, 7, 6, 5, 4, 3, 2, or 1 hours. In certain embodiments, the composition is administered about every 24, 12, 8, 6, or 4 hours. In yet another embodiment, the composition is administered every 8 or 12 hours. In some embodiments, the composition is administered 2, 3, 4, 5, or 6 times during at least one 24 hour period. In another embodiment, the composition is administered 2 or 3 times during at least one 24 hour period. In some embodiments, the composition is administered two times per day (BID), three times per day (TID), four times a day (QID), five times per day, or six times per day. In certain embodiments, the length of treatment can be less than 1 week to 12 months, or more than 12 months. For example, the length of treatment can be from about 1 week to about 4 weeks, from about 2 weeks to about 6 weeks, from about 4 weeks to about 8 weeks, from about 1 month to about 3 months, from about 2 months to about 4 months, from about 3 months to about 6 months, from about 6 months to about 12 months, or more than 12 months. In some embodiments, treatment duration can be until disease remission, for example, from about 1 month to about 24 months, or more than 24 months. In some embodiments, the subject is treated for about 1 month, about 2 months, about 3 months, about 4 months, about 5 months, about 6 months, about 7 months, about 8 months, about 9 months, about 10 months, about 11 months, about 1 year, about 2 years, or more than 2 years. In certain embodiments, the subject is treated indefinitely.

In some embodiments, the effective amount of lithium, or salt thereof, is administered orally, parenterally, transdermally, topically, transmucosally, by inhalation, by suppository, by buccal delivery, by sublingual delivery, by ophthalmic delivery, or by injection (subcutaneous injection, subdermal injection, intramuscular injection, depot administration, or intravenous injection). In certain embodiments, the effective amount of lithium, or salt thereof, is administered orally. In some embodiments, the oral composition is an extended release composition (i.e., designed to slowly release over an extended period of time with a reduction of the peak/trough ratio compared to standard release). Extended release compositions can comprise of sustained-release (SR), or controlled-release (CR) dosage. Sustained-release maintains drug release over a sustained period, but not at a constant rate. Controlled-release maintains drug release over a sustained period at a nearly constant rate. Sustained-release dosage forms are dosage forms designed to release a drug at a predetermined rate in order to maintain a constant drug concentration for a specific period of time with minimum side effects.

In some embodiments, the methods disclosed herein further comprise administering an additional anti-arrhythmic agent. As used herein, additional antiarrhythmic agents, refer to cardiac dysrhythmia medications, and are a group of pharmaceuticals that are used to suppress cardiac arrhythmias, for example, such as premature ventricular contraction (PVC), ventricular premature contraction (VPC), ventricular tachycardia, ventricular fibrillation, paroxysmal supraventricular tachycardia, accessory pathway tachycardia, AV nodal reentrant tachycardia, supraventricular tachycardia, premature atrial contractions, atrial fibrillation, atrial flutter, trigeminy, bigeminy, or Wolff-Parkinson-White (WPW) syndrome. In certain embodiments, the additional anti-arrhythmic agent is a sodium channel blocker (Class I), a beta-blocker (Class II), a potassium channel blocker (Class III), a calcium channel blocker (Class IV), and/or another anti-arrhythmic agent. In some embodiments, about 2.5 mg, about 3.125 mg, about 5 mg, about 6.25 mg, about 10 mg, about 12.5 mg, about 20 mg, about 25 mg, about 30 mg, about 40 mg, about 50 mg, about 60 mg, about 80 mg, about 100 mg, about 150 mg, about 200 mg, about 250 mg, or about 300 mg of the anti-arrhythmic agent can be administered to the subject.

In some embodiments, the additional anti-arrhythmic agent is a beta-blocker (Class II) and the beta-blocker is Acebutolol (SECTRAL®), Atenolol (TENORMIN®), Betaxolol (KERLONE®), Bisoprolol (ZEBETA®, ZIAC®), Carteolol (CARTROL®), Carvedilol (COREG®), Labetalol (NORMODYNE®, TRANDATE®), Metoprolol (LOPRESSOR®, TOPROL-XL®), Nadolol (CORGARD®), Nebivolol (BYSTOLIC®), Penbutolol (LEVATOL®), Pindolol (VISKEN®), Propanolol (INDERAL®), Sotalol (BETAPACE®), or Timolol (BLOCADREN®).

In some embodiments, the additional anti-arrhythmic agent is a sodium channel blocker (Class I) and the sodium channel blocker is Quinidine, Ajmaline, Procainamide, Disopyramide, Lidocaine, Phenytoin, Mexiletine, Tocainide, Encainide, Flecainide, Propafenone, or Moricizine.

In some embodiments, the additional anti-arrhythmic agent is a potassium channel blocker (Class III) and the potassium channel blocker is Amiodarone, Sotalol, Ibutilide, Dofetilide, Dronedarone, E-4031, or Vernakalant.

In some embodiments, the additional anti-arrhythmic agent is a calcium channel blocker (Class IV) and the calcium channel blocker is Verapamil or Diltiazem.

In some embodiments, the additional anti-arrhythmic agent is another anti-arrhythmic agent (for example, a Class V agent) and the another anti-arrhythmic agent is Adenosine, Digoxin, Magnesium citrate, or Magnesium sulfate.

In another aspect, the disclosure provides a composition comprising lithium, or a salt thereof, and an additional anti-arrhythmic agent.

In certain embodiments, lithium, or a salt thereof, can refer to any lithium composition that results in free lithium ($Li^+$) in the serum of a subject when administered to the subject. In certain embodiments of this aspect, the lithium, or salt thereof, is lithium carbonate ($Li_2CO_3$), lithium sulfate ($Li_2SO_4$), lithium citrate ($Li_3C_6H_5O_7$), lithium acetate ($C_2H_3LiO_2$), lithium bromide (LiBr), lithium chloride (LiCl), lithium orotate ($C_5H_3LiN_2O_4$), or lithium gluconate ($C_6H_{11}LiO_7$).

In some embodiments, the additional anti-arrhythmic agent is a sodium channel blocker (Class I), a beta-blocker (Class II), a potassium channel blocker (Class III), a calcium channel blocker (Class IV), and/or another anti-arrhythmic agent.

In some embodiments, the additional anti-arrhythmic agent is a beta-blocker and the beta-blocker is Acebutolol (SECTRAL®), Atenolol (TENORMIN®), Betaxolol (KERLONE®), Bisoprolol (ZEBETA®, ZIAC®), Carteolol (CARTROL®), Carvedilol (COREG®), Labetalol (NORMODYNE®, TRANDATE®), Metoprolol (LOPRESSOR®, TOPROL-XL®), Nadolol (CORGARD®), Nebivolol (BYSTOLIC®), Penbutolol (LEVATOL®), Pindolol (VISKEN®), Propanolol (INDERAL®), Sotalol (BETAPACE®), or Timolol (BLOCADREN®).

In some embodiments, the additional anti-arrhythmic agent is a sodium channel blocker (Class I) and the sodium channel blocker is Quinidine, Ajmaline, Procainamide, Disopyramide, Lidocaine, Phenytoin, Mexiletine, Tocainide, Encainide, Flecainide, Propafenone, or Moricizine.

In some embodiments, the additional anti-arrhythmic agent is a potassium channel blocker (Class III) and the potassium channel blocker is Amiodarone, Sotalol, Ibutilide, Dofetilide, Dronedarone, E-4031, or Vernakalant.

In some embodiments, the additional anti-arrhythmic agent is a calcium channel blocker (Class IV) and the calcium channel blocker is Verapamil or Diltiazem.

In some embodiments, the additional anti-arrhythmic agent is another anti-arrhythmic agent (for example, a Class V agent) and the another anti-arrhythmic agent is Adenosine, Digoxin, Magnesium citrate, or Magnesium sulfate.

In one embodiment, the lithium, or salt thereof, is lithium carbonate ($Li_2CO_3$), and the beta-blocker is Metoprolol (LOPRESSOR®, TOPROL-XL®). In another embodiment, the lithium, or salt thereof, is lithium sulfate ($Li_2SO_4$), and the beta-blocker is Metoprolol (LOPRESSOR®, TOPROL-XL®).

In some embodiments, the composition comprises about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 110 mg, about 120 mg, about 125 mg, about 130 mg, about 140 mg, about 150 mg, about 160 mg, about 170 mg, about 175 mg, about 180 mg, about 190 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, or about 1800 mg of the lithium, or salt thereof.

In some embodiments, the composition comprises about 2.5 mg, about 3.125 mg, about 5 mg, about 6.25 mg, about 10 mg, about 12.5 mg, about 20 mg, about 25 mg, about 30 mg, about 40 mg, about 50 mg, about 60 mg, about 80 mg, about 100 mg, about 150 mg, about 200 mg, about 250 mg, or about 300 mg of the additional anti-arrhythmic agent.

In some embodiments, the composition is a "pharmaceutical composition" or "therapeutic composition." The terms "pharmaceutical composition" or "therapeutic composition" as used herein refer to a compound or composition capable of inducing a desired therapeutic effect when properly administered to a patient. For example, in a patient with an arrhythmia, administration of a therapeutic composition would result in disappearance of or a decrease in the arrhythmia in the patient. In another example, in a patient with PVCs, administration of a therapeutic composition would result in disappearance of or a decrease in the number of PVCs the patient experiences.

The pharmaceutical composition can contain formulation materials for modifying, maintaining, or preserving, for example, the pH, osmolarity, viscosity, clarity, color, isotonicity, odor, sterility, stability, rate of dissolution or release, adsorption, or penetration of the composition. Suitable formulation materials include, but are not limited to, amino acids (such as glycine, glutamine, asparagine, arginine, or lysine), antimicrobials, antioxidants (such as ascorbic acid, sodium sulfite, or sodium hydrogen-sulfite), buffers (such as borate, bicarbonate, Tris-HCl, citrates, phosphates, or other organic acids), bulking agents (such as mannitol or glycine), chelating agents (such as ethylenediamine tetraacetic acid (EDTA)), complexing agents (such as caffeine, polyvinylpyrrolidone, beta-cyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorb ate 80; triton; tromethamine; lecithin; cholesterol or tyloxapal), stability enhancing agents (such as sucrose or sorbitol), tonicity enhancing agents (such as alkali metal halides—preferably sodium or potassium chloride—or mannitol sorbitol), delivery vehicles, diluents, excipients and/or pharmaceutical adjuvants (see, e.g., REMINGTON'S PHARMACEUTICAL SCIENCES (18th Ed., A. R. Gennaro, ed., Mack Publishing Company 1990), and subsequent editions of the same, incorporated herein by reference for any purpose).

In some embodiments, the compositions as disclosed herein can be administered orally, parenterally, transdermally, topically, transmucosally, by inhalation, by suppository, by buccal delivery, by sublingual delivery, by ophthalmic delivery, or by injection (subcutaneous injection, subdermal injection, intramuscular injection, depot administration, or intravenous injection). In certain embodiments, the composition is administered orally. In some embodiments, the oral composition is an extended release composition (i.e., designed to slowly release over an extended period of time). Extended release compositions can comprise of sustained-release (SR), or controlled-release (CR) dosage. Sustained-release maintains drug release over a sustained period, but not at a constant rate. Controlled-release maintains drug release over a sustained period at a nearly constant rate. Sustained-release dosage forms are dosage forms designed to release a drug at a predetermined rate in order to maintain a constant drug concentration for a specific period of time with minimum side effects.

EXAMPLES

The Examples that follow are illustrative of specific embodiments of the disclosure as provided herein, and various uses thereof. They are set forth for explanatory purposes only, and should not be construed as limiting the scope of the disclosure as provided herein in any way.

Example 1: Treatment of PVCs Using Lithium

A patient with PVCs as documented with a cardiac event monitor was given lithium carbonate 300 mg per day ($Li_2CO_3$ 150 mg BID; resulting in a lithium serum level of about 0.2) in combination with metoprolol 150 mg per day. Within a few days, PVCs were reduced by about 90% (observation by EKG by physician/patient) for the duration of treatment with lithium. Three trials were performed with lithium carbonate (300 mg per day, 150 mg BID) in combination with metoprolol 150 mg per day, and for each trial, PVCs were reduced by at least 90% for the duration of treatment with lithium. Within about one week of discontinuing lithium treatment, PVCs recurred. In each of three trials of lithium 150 mg twice daily, the number of PVCs was reduced within 12 days of starting the lithium by 95% of the pre-lithium number of PVCs, and the number of PVCs was reduced within 22 days of starting the lithium to 2 PVCs per minute or none (note: 2 PVCs per minute is clinically insignificant for anyone). The rate of 2 PVCs per minute or none was maintained in the trials until the lithium was discontinued. The first trial was 109 days. The second trial was 43 days. In the third trial, the number of PVCs of less than 2 per minute has been maintained for 54 days (as of Aug. 26, 2020). See FIG. 1.

Example 2: Treatment of PVCs Using Lithium

A patient with PVCs as documented with a cardiac event monitor is given lithium (as lithium carbonate, lithium citrate or lithium sulphate) 300 mg per day in an extended release formulation in combination with metoprolol 50 mg per day—every twelve to twenty-four hours (e.g., lithium carbonate 300 mg and metoprolol 50 mg once daily or lithium carbonate 150 mg and metoprolol 25 mg every twelve hours). Three days after treatment is initiated, a lithium blood level is obtained. A repeat cardiac event monitor is performed fourteen days after starting treatment. It is expected a patient's PVCs will be reduced by at least 90%. If PVCs are not reduced, then the lithium dose is to be adjusted, and another blood level obtained after three days. A repeat cardiac event monitor is performed in fourteen days. The process of dose adjustment, blood lithium levels, and cardiac event monitor is repeated until there is a 90% or greater reduction in PVCs. When that is obtained, another cardiac event monitor is done in one month. A further reduction in PVCs (to an amount of no more than 2 per minute) is expected, but will not be necessary as long as the previous reduction of 90% in PVCs is maintained.

All references cited in this application are expressly incorporated by reference herein.

The invention claimed is:

1. A method for treating premature ventricular contraction (PVC) or ventricular premature contraction (VPC), consisting of administering an effective amount of a lithium salt to a subject in need thereof, wherein the lithium salt is lithium carbonate ($Li_2CO_3$), lithium sulfate ($Li_2SO_4$), lithium citrate ($Li_3C_6H_5O_7$), lithium acetate ($C_2H_3LiO_2$), lithium bromide (LiBr), lithium chloride (LiCl), lithium orotate ($C_5H_3LiN_2O_4$), or lithium gluconate ($C_6H_{11}LiO_7$).

2. The method of claim 1, wherein the effective amount of the lithium salt comprises about 5 mg to about 1800 mg per day, about 10 mg to about 1200 mg per day, about 25 mg to about 600 mg per day, about 50 mg to about 550 mg per day, about 100 mg to about 500 mg per day, about 150 mg to about 450 mg per day, about 200 mg to about 400 mg per day, or about 250 mg to about 350 mg per day.

3. The method of claim 2, wherein the effective amount of the lithium salt comprises about 300 mg per day.

4. The method of claim 1, wherein the effective amount of the lithium salt results in a lithium ($Li^+$) serum concentration in the subject in the range of about 0.01 to about 1.2 mmol/L, about 0.02 to about 1.0 mmol/L, about 0.05 to about 0.8 mmol/L, about 0.1 to about 0.6 mmol/L, about 0.2 to about 0.5 mmol/L, about 0.25 to about 0.45 mmol/L, or about 0.1 to about 0.3 mmol/L.

5. The method of claim 1, wherein the effective amount of the lithium salt results in a lithium ($Li^+$) serum concentration in the subject in the range of about 0.1 to about 0.3 mmol/L.

6. The method of claim 1, wherein the effective amount of the lithium salt is administered as an extended release formulation.

7. The method of claim 1, wherein the effective amount of the lithium salt is administered one time per day, two times per day, three times per day, or four times per day.

8. The method of claim 1, wherein the effective amount of the lithium salt is administered orally, parenterally, transdermally, topically, transmucosally, by inhalation, by suppository, by buccal delivery, by sublingual delivery, by ophthalmic delivery, or by injection (subcutaneous injection, subdermal injection, intramuscular injection, depot administration, or intravenous injection).

9. The method of claim 1, wherein the subject is treated for about 1 month, about 2 months, about 3 months, about 4 months, about 5 months, about 6 months, about 7 months, about 8 months, about 9 months, about 10 months, about 11 months, about 1 year, about 2 years, or more than 2 years.

10. The method of claim 1, wherein the subject is treated indefinitely.

* * * * *